United States Patent
Stockmans et al.

(10) Patent No.: US 10,799,365 B1
(45) Date of Patent: Oct. 13, 2020

(54) BONE JOINT IMPLANTS

(71) Applicant: Loci Orthopaedics Limited, Upper Newcastle, Galway (IE)

(72) Inventors: Filip Stockmans, Heule Kortrijk (BE); Gerry Clarke, County Galway (IE); Arnold-Peter C. Weiss, Barrington, RI (US); Amy L. Ladd, Stanford, CA (US); Brendan Boland, County Kildare (IE)

(73) Assignee: Loci Orthopaedics Limited, Upper Newcastle, Galway (IE)

( * ) Notice: Subject to any disclaimer, the term of this patent is extended or adjusted under 35 U.S.C. 154(b) by 0 days.

(21) Appl. No.: 16/678,552

(22) Filed: Nov. 8, 2019

Related U.S. Application Data

(60) Provisional application No. 62/823,392, filed on Mar. 25, 2019, provisional application No. 62/823,367, filed on Mar. 25, 2019.

(51) Int. Cl.
*A61F 2/42* (2006.01)
*A61F 2/30* (2006.01)

(52) U.S. Cl.
CPC .......... *A61F 2/4241* (2013.01); *A61F 2/4261* (2013.01); *A61F 2002/3006* (2013.01); *A61F 2002/30663* (2013.01); *A61F 2002/30685* (2013.01); *A61F 2002/30935* (2013.01); *A61F 2002/4258* (2013.01)

(58) Field of Classification Search
CPC .................. A61F 2/4241; A61F 2002/4258
See application file for complete search history.

(56) References Cited

U.S. PATENT DOCUMENTS

| | | | |
|---|---|---|---|
| 3,916,451 A | 11/1975 | Buechel et al. | |
| 4,156,296 A * | 5/1979 | Johnson | A61F 2/4225 623/21.19 |
| 4,213,208 A | 7/1980 | Marne | |
| 4,304,011 A * | 12/1981 | Whelan, III | A61F 2/4241 623/21.16 |
| 4,685,919 A | 8/1987 | Niwa et al. | |

(Continued)

FOREIGN PATENT DOCUMENTS

| | | |
|---|---|---|
| CN | 103815989 A | 5/2014 |
| EP | 0322493 A1 | 7/1989 |

(Continued)

OTHER PUBLICATIONS

European Search Report for European Application No. 19167519.8, dated Sep. 12, 2019 (7 pages).

(Continued)

*Primary Examiner* — Bruce E Snow
*Assistant Examiner* — Melissa A Hoban
(74) *Attorney, Agent, or Firm* — Bookoff McAndrews, PLLC

(57) ABSTRACT

Bone joint implants are described herein. The bone joint implants may comprise a metallic proximal platform configured for translational motion on the trapezium bone; a distal stem configured for intramedullary engagement with an end of the first metacarpal bone; an articulating coupling between the proximal platform and distal stem; and a proximal non-metallic wear surface and a distal non-metallic wear surface.

10 Claims, 8 Drawing Sheets

(56) References Cited

U.S. PATENT DOCUMENTS

| | | | |
|---|---|---|---|
| 4,955,916 A * | 9/1990 | Carignan | A61F 2/4241 623/21.16 |
| 5,147,386 A | 9/1992 | Carignan et al. | |
| 5,405,400 A * | 4/1995 | Linscheid | A61F 2/4241 623/21.15 |
| 5,458,601 A | 10/1995 | Young et al. | |
| 5,507,822 A * | 4/1996 | Bouchon | A61F 2/4241 623/21.16 |
| 5,593,445 A | 1/1997 | Waits | |
| 5,702,469 A * | 12/1997 | Whipple | A61F 2/4241 623/21.15 |
| 6,126,690 A * | 10/2000 | Ateshian | A61F 2/30942 623/22.4 |
| 6,206,925 B1 | 3/2001 | Tornier | |
| 7,011,686 B2 | 3/2006 | Ball et al. | |
| 8,303,664 B1 | 11/2012 | Burstein et al. | |
| 2005/0033426 A1 | 2/2005 | Ogilvie et al. | |
| 2006/0041314 A1 | 2/2006 | Millard | |
| 2006/0074492 A1 | 4/2006 | Frey | |
| 2008/0221698 A1 | 9/2008 | Berger | |
| 2008/0269908 A1 * | 10/2008 | Warburton | A61B 17/1782 623/21.15 |
| 2009/0112328 A1 | 4/2009 | Tornier et al. | |
| 2010/0010637 A1 | 1/2010 | Pequignot | |
| 2013/0150975 A1 | 6/2013 | Iannotti et al. | |
| 2013/0197655 A1 | 8/2013 | Scheker | |
| 2013/0338784 A1 | 12/2013 | Pallia | |
| 2014/0074246 A1 | 3/2014 | Huebner | |
| 2014/0128984 A1 * | 5/2014 | Jou | A61F 2/4241 623/21.15 |
| 2017/0224499 A1 * | 8/2017 | Clarke | A61F 2/4241 |
| 2018/0214276 A1 | 8/2018 | Humphrey | |
| 2019/0167437 A1 | 6/2019 | Clarke et al. | |

FOREIGN PATENT DOCUMENTS

| | | |
|---|---|---|
| EP | 2749256 A1 | 7/2014 |
| EP | 3205311 A1 | 8/2017 |
| FR | 2 805 152 A1 | 8/2001 |
| FR | 2805151 A1 | 8/2001 |
| FR | 2900045 A1 | 10/2007 |
| FR | 2912051 A1 | 8/2008 |
| FR | 2 931 059 A1 | 11/2009 |
| FR | 3 027 213 A1 | 4/2016 |
| WO | WO 2014/077750 A1 | 5/2014 |
| WO | WO 2015/088403 A1 | 6/2015 |
| WO | WO 2017/137607 A2 | 8/2017 |

OTHER PUBLICATIONS

International Search Report and Written Opinion for International Application No. 2019/0058, completed Jun. 25, 2019 (8 pages).

International Search Report and Written Opinion for International Application No. PCT/EP2017/053079, dated Aug. 23, 2017 (11 pages).

Crisco, J. et al., "In Vivo Kinematics of the Trapeziometacarpal Joint During Thumb Extension-Flexion and Abduction-Adduction," J Hand Surg Am., 2015, vol. 40 (2) 289-96.

De Aragon, J.S.M. et al., "Early Outcomes of Pyrolytic Carbon Hemiarthroplasty for the Treatment of Trapezial-Metacarpal Arthritis," J Hand Surg Am., 2009, vol. 34A (2) 205-12.

Krukhaug, Y. et al., "The results of 479 thumb carpometacarpal joint replacements reported in the Norwegian Arthroplasty Register," J Hand Surg Am., 2014, vol. 39 (8) 1-7, http://jhs.sagepub.com/content/early/2014/04/29/1753193413513988.

Naidu, S.H. et al., "Titanium Based Joint Arthroplasty: A Finite Element Analysis and Clinical Study," J Hand Surg Am., 2006, vol. 31 (5) 760-65.

Pritchett, J.W. et al., "A Promising Thumb Basal Joint Hemiarthroplasty for Treatment of Trapeziometacarpal Osteoarthritis," Clinical Orthopaedics and Related Research, 2012, vol. 470 (10) 2756-63.

Turker, T. et al., "Trapezio-metacarpal arthritis: The price of an opposable thumb!," Indian Journal of Plastic Surgery, 2011, vol. 44 (22) 308-16.

"TIE-IN™ Trapezium Implant—A Comprehensive Solution for CMC," Wright Medical Group N.V., Jul. 30, 2016.

Summary of Safety and Effectiveness, TIE-IN™ Trapezium, Wright Medical Group, Nov. 7, 2003.

International Search Report and Written Opinion for International Application No. PCT/EP2020/055344, dated May 13, 2020 (12 pages).

International Search Report and Written Opinion for International Application No. PCT/EP2020/055353, dated May 13, 2020 (6 pages).

* cited by examiner

Brown TD, Callaghan JJ. Impingement in Total Hip Replacement: Mechanisms and Consequences. Curr Orthop. 2008;22(6):376-391.

Brown TD, Callaghan JJ. Impingement in Total Hip Replacement: Mechanisms and Consequences. Curr Orthop. 2008;22(6):376-391. shows a 3D Finite Element model of total hip dislocation.

Section A-A

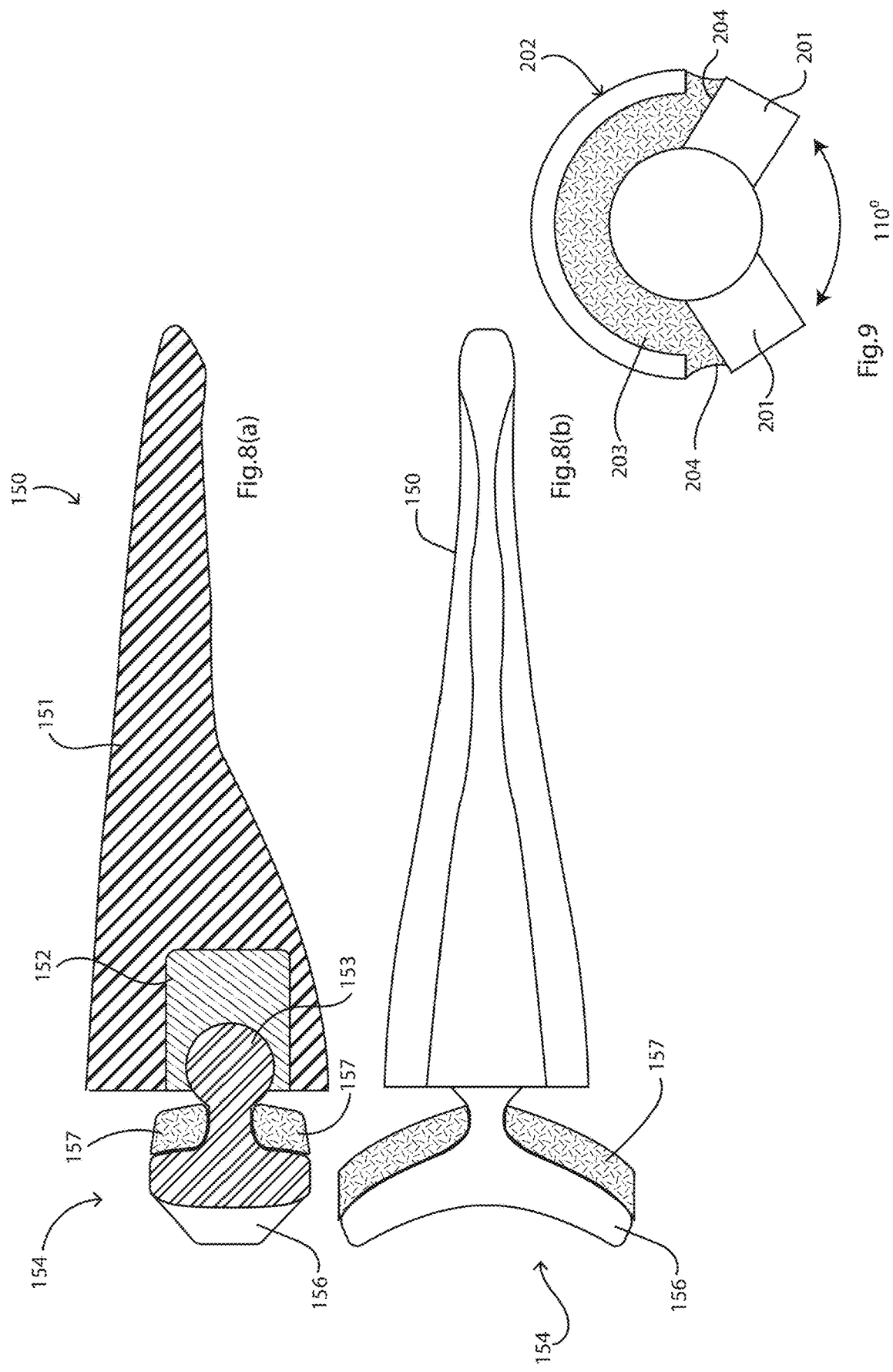

BONE JOINT IMPLANTS

CROSS-REFERENCE TO RELATED APPLICATIONS

This application claims the benefit of priority of U.S. Provisional Application Nos. 62/823,367 and 62/823,392, both filed on Mar. 25, 2019, all of which are incorporated herein by reference in their entireties

INTRODUCTION

The invention relates to an implant for a bone joint. In some examples it relates to implants in which there are multiple axes of rotation, such as those in which there is a dual axis hemiarthroplasty with two axes of rotation such as in the hand or elbow. However, in other aspects the invention relates to a uni-axial implant such as a hip joint implant.

An example of an implant with multiple axes of rotation is one for a first carpometacarpal joint for spacing a trapezium bone from a first metacarpal bone. In this case there is translational motion of a saddle-shaped surface of a proximal implant part over the trapezium and three-dimensional rotational movement of the distal part due to an articulated coupling such as a ball-and-socket joint. An example of such an implant is described in WO2017/137607 (NUIG).

In such an implant the point of motion may be at, or between, two points, concurrently or independently. Depending on the biomechanics of the joints into which the implant has been inserted the main force of motion may change rapidly and abruptly between the two points. FIGS. 1(*a*) and (*b*) illustrate a dual axis implant providing two axes of rotation: Ab-Ad (Axis 1) in the base of the metacarpal and Ex-Fl (Axis 2) over the surface of the trapezium to recreate the native axes of rotation of the joint. A radiolucent stem is used in FIG. 1(*a*) to demonstrate the location of the ball and socket in the metacarpal.

Impingement in an orthopaedic implant may be caused any time there is a decrease in the space between the two elements causing one element to impact on the other, for example, the head of an articulating hemiarthroplasty impinging on the stem.

Uncontrolled impingement is a cause of poor outcomes of implants. Referring also to uni-axial implants such as prosthetic hip arthroplasty; it can lead to instability, accelerated wear, and unexplained pain. Impingement is influenced by prosthetic design, component position, biomechanical factors, and patient variables. Uncontrolled impingement is linked to dislocation and accelerated wear comes from implant retrieval studies. Operative principles that maximize an impingement-free range of motion include correct combined acetabular and femoral anteversion and an optimal head-neck ratio. Operative techniques for preventing impingement include medialization of the cup to avoid component impingement and restoration of hip offset and length to avoid osseous impingement.

To illustrate these problems FIG. 1 (*c*) is an image from Brown T D, Callaghan J J. Impingement in Total Hip Replacement: Mechanisms and Consequences. Curr Orthop. 2008; 22(6):376-391. These images show Finite Element Analysis of a constrained-liner THA, showing stress contours at the instant of incipient dislocation (A, B). FIG. 1(*d*), also from Brown T D, Callaghan J J. Impingement in Total Hip Replacement: Mechanisms and Consequences. Curr Orthop. 2008; 22(6):376-391, shows a 3D Finite Element model of total hip dislocation, illustrating the initial relative position of the implant components (left), the acetabular component bearing surface stress during stable articulation (centre), and the corresponding stresses just prior to a posterior dislocation event (right).

The invention is directed towards providing an improved implant with controlled impingement, or at least reduced effects if impingement occurs.

SUMMARY OF THE INVENTION

The present disclosure includes bone joint implants. For example, the present disclosure includes a bone joint implant for a mammalian first carpometacarpal joint comprising a metallic proximal platform configured for translational motion on the trapezium bone; a distal stem configured for intramedullary engagement with an end of the first metacarpal bone; an articulating coupling between the proximal platform and distal stem; and a proximal non-metallic wear surface and a distal non-metallic wear surface.

According to some examples herein, the proximal non-metallic wear surface may form a buffer surface that prohibits contact between the proximal platform and the stem during articulation; may include a concave curvature; and/or may form an annular surface. The proximal platform may include a distal end surface having a convex curvature. In at least one example, the distal non-metallic wear surface may be spherically shaped.

In some examples, the implant may include a unitary non-metallic wear member, and the proximal non-metallic wear surface and the distal non-metallic wear surface may be formed on the unitary wear member. The unitary non-metallic wear member may be an insert received in a proximal end surface of the stem, and the insert may include a proximal portion extending proximally of the proximal end surface of the stem. In some examples, the proximal portion may be a flange of the insert and the flange may include the proximal non-metallic wear surface, and/or the articulating coupling may be a ball and socket coupling, and the insert may form the socket of the ball and socket coupling.

The present disclosure also includes a bone joint implant for a mammalian first carpometacarpal joint, comprising a proximal part configured for translational motion on the trapezium bone, the proximal part including a platform; a distal part configured for intramedullary engagement with an end of the first metacarpal bone, the distal part including a stem and a wear surface located proximal the stem; and an articulating coupling between the proximal and distal parts, the wear surface being further located to limit articulation and prohibit contact between the platform and the stem. In at least one example, the wear surface may be non-metallic and the platform may be metallic. The wear surface may include a concave curvature and/or may form an annular surface. The platform may include a distal end surface having a convex curvature.

In some examples, the implant may include an insert received in a proximal end surface of the stem, wherein the wear surface is formed on the insert. The insert may include a proximal flange, wherein the wear surface is formed on the flange. Additionally, the articulating coupling may be a ball and socket coupling, and the ball may form a part of the proximal part, and the socket may be formed by the insert. In at least one example, the ball may extend distally of the flange.

The present disclosure also includes a bone joint implant for a mammalian first carpometacarpal joint, comprising a proximal part configured for translational motion on the trapezium bone, the proximal part including a platform; a distal part configured for intramedullary engagement with an end of the first metacarpal bone, the distal part including a stem and an insert extending into a proximal end of the stem, the insert including a flange extending proximal of the proximal end of the stem; and an articulating coupling between the proximal and distal parts, and the flange including a proximal end surface limiting movement between the proximal part and the distal part. In at least one example, the insert may be non-metallic and the platform may be metallic. The proximal end surface of the flange may have a concave curvature and/or the platform may include a distal end surface having a convex curvature. In at least one example, the flange may be annular. Additionally, the articulating coupling may be a ball and socket coupling, the proximal part may include the ball and the insert may include the socket, and/or the ball may extend distally of the flange.

The present disclosure also includes a bone joint implant for a mammalian first carpometacarpal joint, comprising a proximal part configured for translational motion on the trapezium bone, the proximal part including a metallic platform having a proximal end surface having a concave curvature, and a distal end surface having a convex curvature; a distal part configured for intramedullary engagement with an end of the first metacarpal bone, the distal part including a metallic stem and a non-metallic insert extending into a proximal end of the stem, the insert including a flange extending proximal of the proximal end of the stem; and a ball and socket coupling between the proximal and distal parts, the proximal part including the ball, and the insert including the socket, and the flange including a proximal end surface limiting movement between the proximal part and the distal part. According to some examples, the proximal end surface may include a concave surface and/or the proximal end surface may be annular.

DETAILED DESCRIPTION OF THE INVENTION

The invention will be more clearly understood from the following description of some embodiments thereof, given by way of example only with reference to the accompanying drawings in which:

FIGS. 1(*a*) and 1(*b*) are diagrams showing in the prior art different axes of motion for an implant for a first carpometacarpal joint for spacing a trapezium bone from a first metacarpal bone, as discussed above in the Introduction;

Figure 7A:
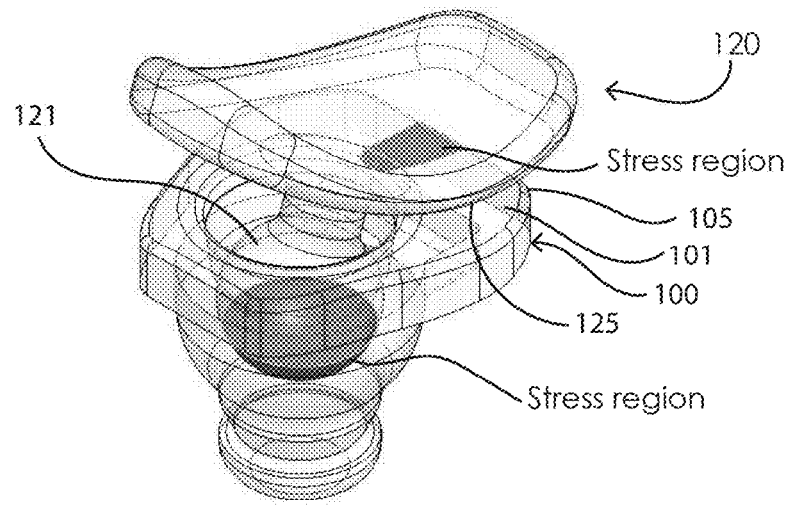
Figure 7B:
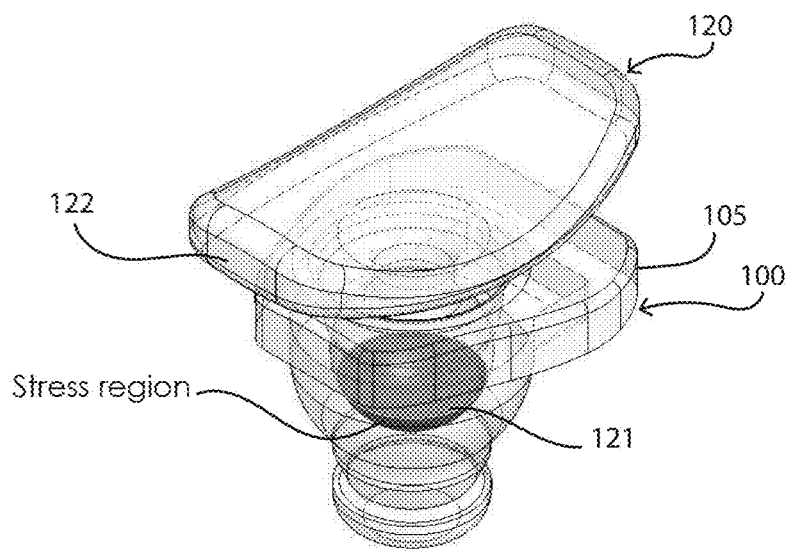

FIGS. 7(*a*) and 7(*b*) illustrate cross-sectional views of an implant, showing the areas of material stress;

FIGS. 8(*a*) and 8(*b*) are sectional views showing an implant with an interface coating on the proximal part; and FIG. 9 is a cross-sectional view of an implant for a hip joint, with a flange to increase surface area to reduce contact stresses.

TERMS

"Intramedullary engagement" means engagement within a medullary cavity formed or existing in the bone, where the cavity is generally but not exclusively formed along a longitudinal axis of the bone. In one embodiment, the intramedullary engagement fixture comprises a screw or nail or interference-fit stem, although other intramedullary fixtures are known. Typically, the screw is externally threaded. Intramedullary fixtures are sold by Smith & Nephew, Zimmer, Synthes and other suppliers. The engagement anchors the implant to the bone. In one embodiment, the medullary cavity is formed in a position that is offset towards a volar direction. The medullary cavity may be formed in a position offset from the anatomical and or biomechanical axis of the bone.

Figure 2:
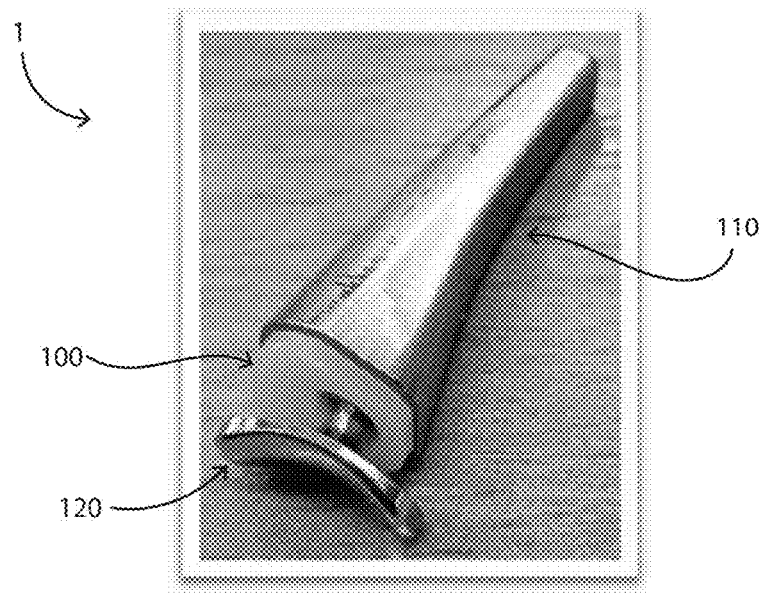
FIG. 2 is an image showing in perspective an implant of the invention, both proximal and distal parts.
Figure 3A:
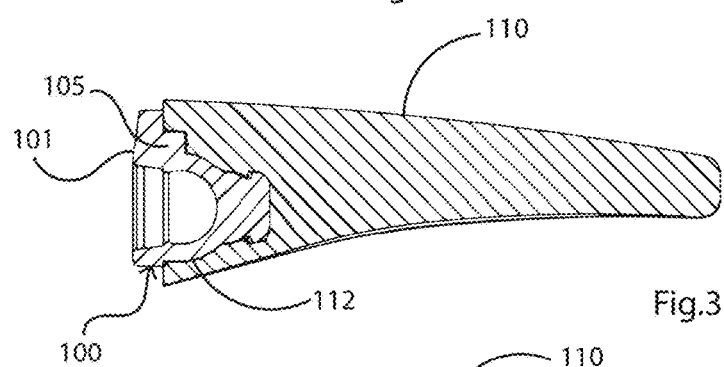
FIG. 3(*a*) is a cross-sectional view through the implant distal part, and FIG. 3(*b*) is a perspective view of the stem of the distal part, FIG. 3(*c*) is a perspective view of the complete distal part, and FIG. 3(*d*) is a perspective view of the proximal part.
Figure 3B:
Figure 3C:
Figure 3D:
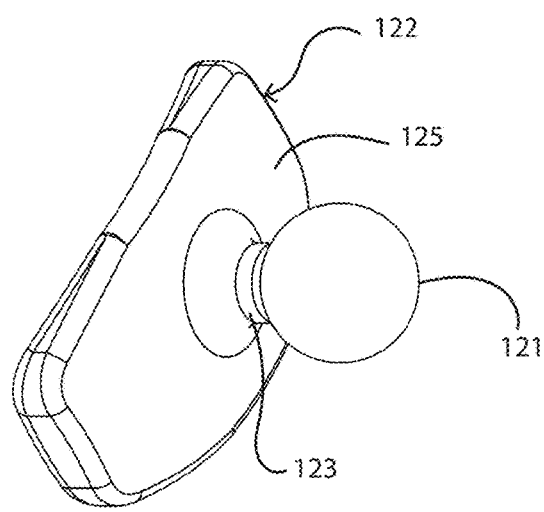
Figure 4:
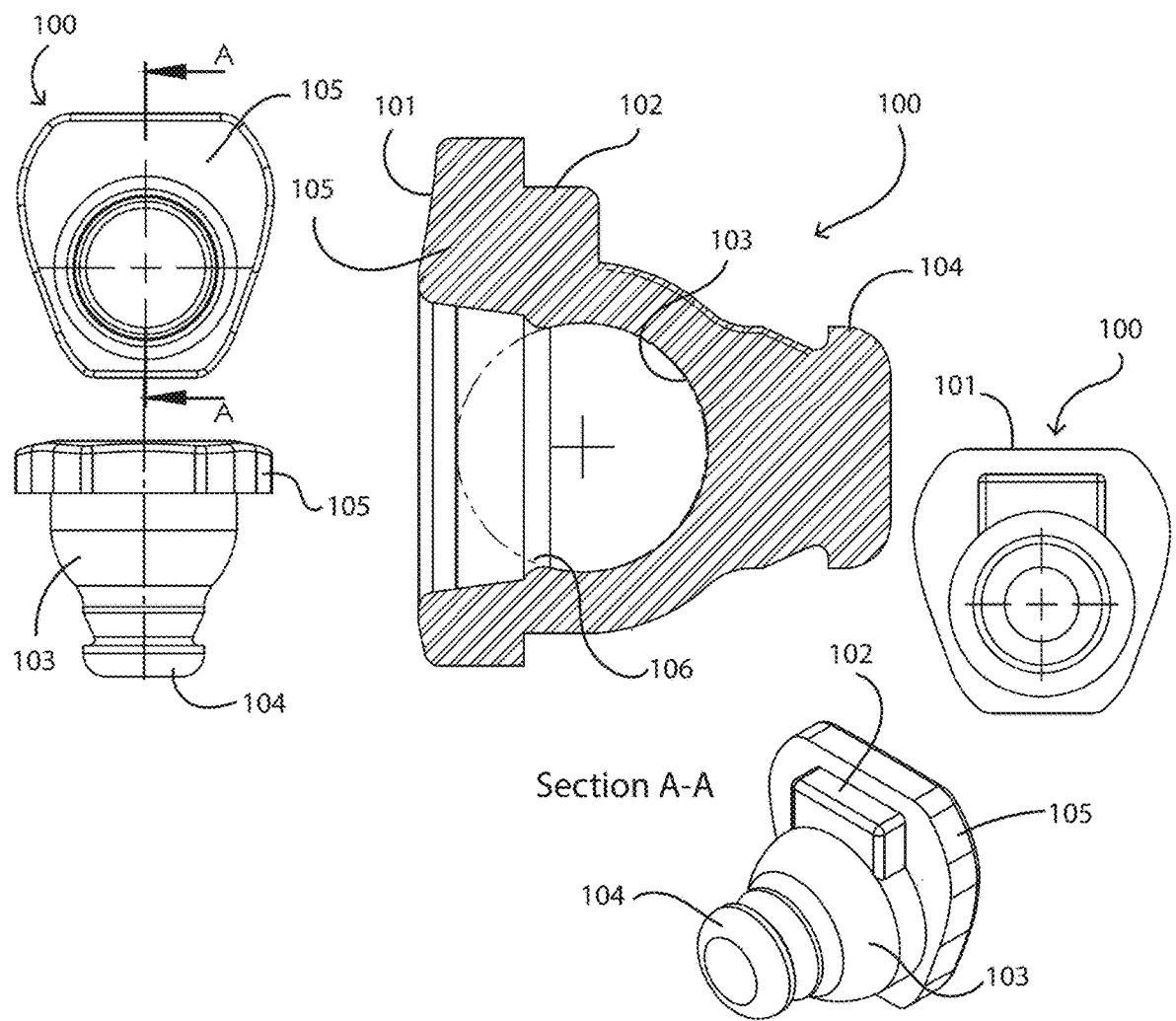
FIG. 4 is a set of views showing a portion of the distal part of the implant, including top plan, end, perspective, and cross-sectional views.

"Non-engaging abutment" means that the proximal part is not fixed to the first bone, but is configured to abut the end of the bone in a manner that allows translational movement thereof. How this is achieved depends on the joint being treated and the specific anatomy of the first bone. As an example, when the joint is a carpometacarpal joint in the thumb, the end of the trapezium bone has a twisted saddle shape (see FIG. 2 of Turker et al, Indian J Plast Surg. 2011, 44(2): 308-316) and the platform is configured to rest upon this saddle and allow translational movement of the platform across the saddle. Thus, in this embodiment, the curved saddle-shaped platform typically has a concave-convex shape, which has a concave curvature along a longitudinal aspect, and a convex curvature along a lateral aspect. The curved saddle-shaped platform may have a concave and convex curvature in both the longitudinal and lateral aspects, i.e., both the length and width directions (as shown in the figures, e.g., FIGS. 2 and 4). This shape has been shown to provide an engagement that closely mimics the physiological situation and allows for natural flexion-extension articulation. When discussing curvature in this disclosure (e.g. concave or convex), the point of reference is from outside the structure (implant) or component, not from inside the structure or component.

"Translational movement of the second bone in relation to the first bone" means non-pivoting movement of the second bone in relation to the first bone. This can also be described as sliding movement. An example is the involuntary translational movement of the metacarpal in relation to the trapezium in the thumb carpometacarpal joint, which contributes significantly to extension-flexion articulation of the thumb. The implant of the invention facilitates such translational movement by employing a proximal part that is configured to non-engagingly abut the first bone.

"Articulating coupling" means a coupling that allows articulation between the first and second parts of the implant. The specific type of coupling employed in the implant depends on the joint that is being treated with the implant, and in some cases the indication or severity of the indication. For example, when the implant is for treatment of an arthritic hinge joint, for example an elbow joint, the implant will generally comprise a hinge joint coupling. When the implant is for treatment of a saddle joint, for example a carpometacarpal joint, the implant will generally comprise a ball and socket joint or a universal joint. "Controlled articulation" means that the articulation is constrained to specific types of articulation.

"Abutting platform" means a base that abuts the end of the first bone (for example the end of the trapezium) so that translational (i.e. sliding) movement of the platform in relation to the end of the bone is allowed. The bone is not fixed to the platform. The platform may be configured to conform to a surface of the top of the bone. In one embodiment, the platform is shaped to mimic an end of the second bone, so as to allow the same range of movements as the natural healthy joint, including translational movement. In the case of the carpometacarpal joint, where the end of the first bone (trapezium) has a twisted saddle topography, the platform may be shaped to conform to the twisted saddle to allow one or more or all of the following range of movements of the first metacarpal in relation to the trapezium, flexion, extension, abduction, adduction, internal rotation, external rotation, opposition, circumduction, and translation.

DESCRIPTION OF THE EMBODIMENTS

Referring to FIGS. 2 to 7 an implant 1 has a distal part with an insert 100 in a stem 110, and a proximal part 120.

Figure 1A:
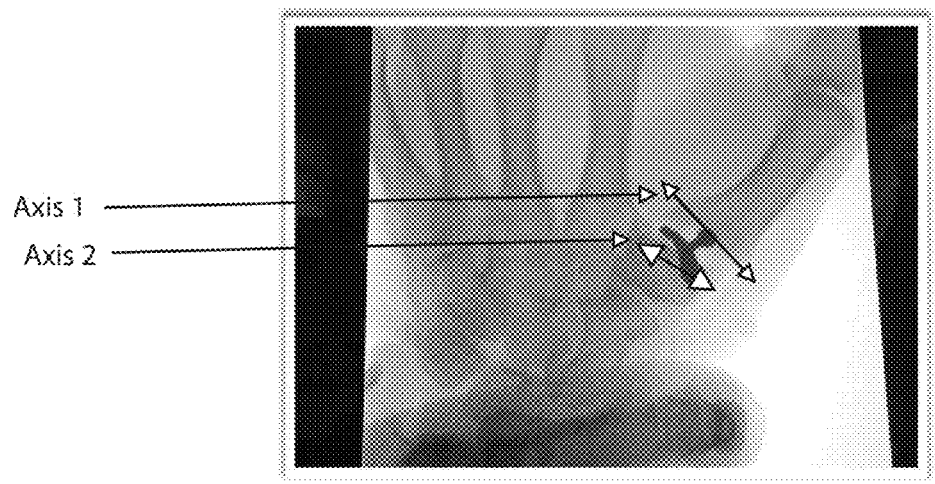
FIG. 1(*c*) is a Finite Element Analysis (FEA) diagram showing prior art impingement in a hip joint, and FIG. 1(*d*) is an FEA diagram also of a hip joint showing impingement and egress sites in the prior art, also as discussed above in the Introduction.
Figure 1B:
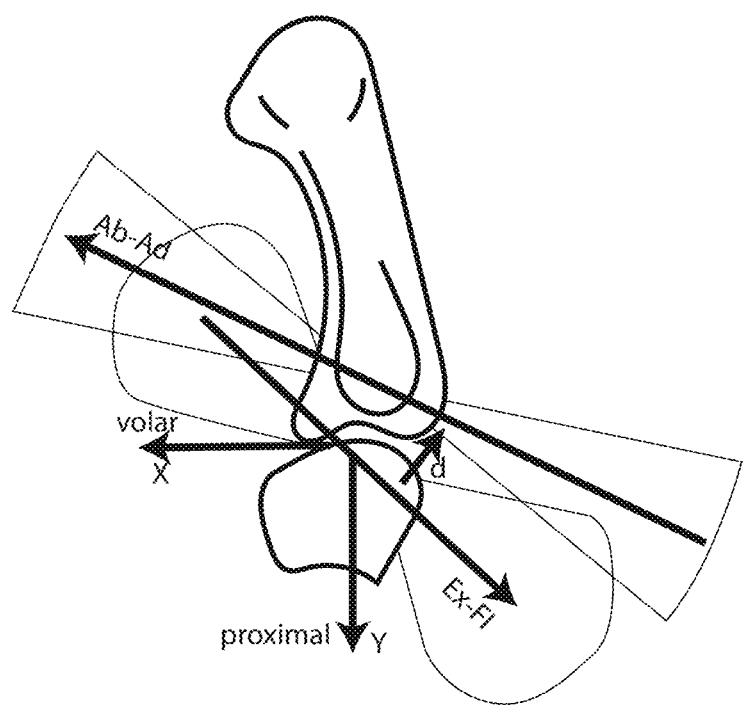
Figure 1C:
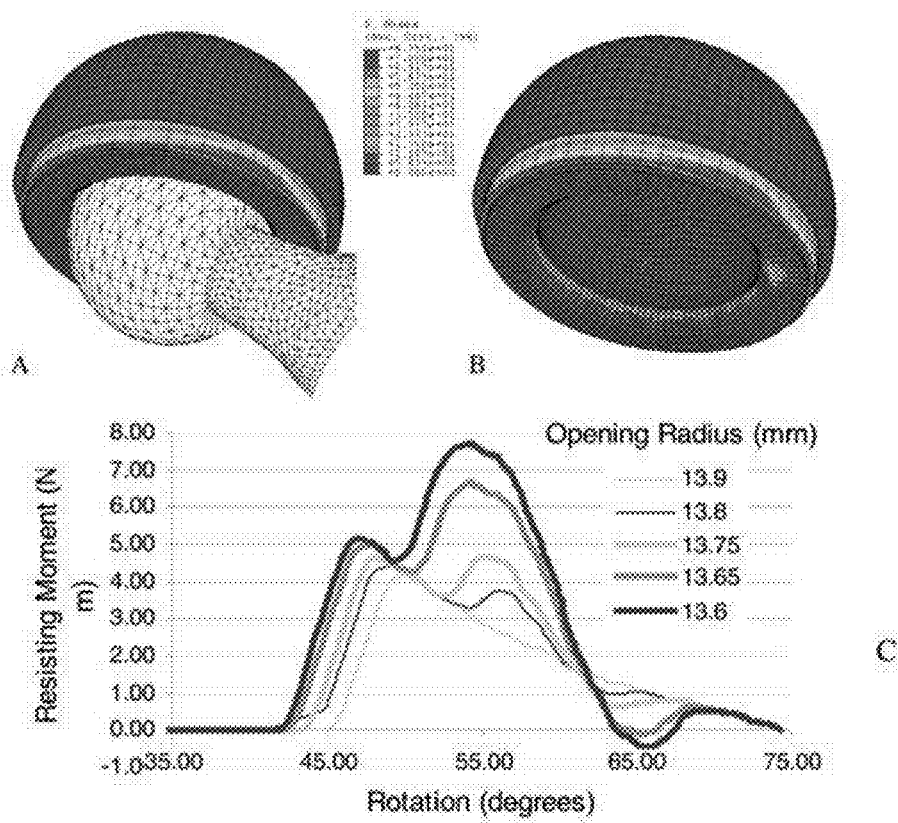
Figure 1D:
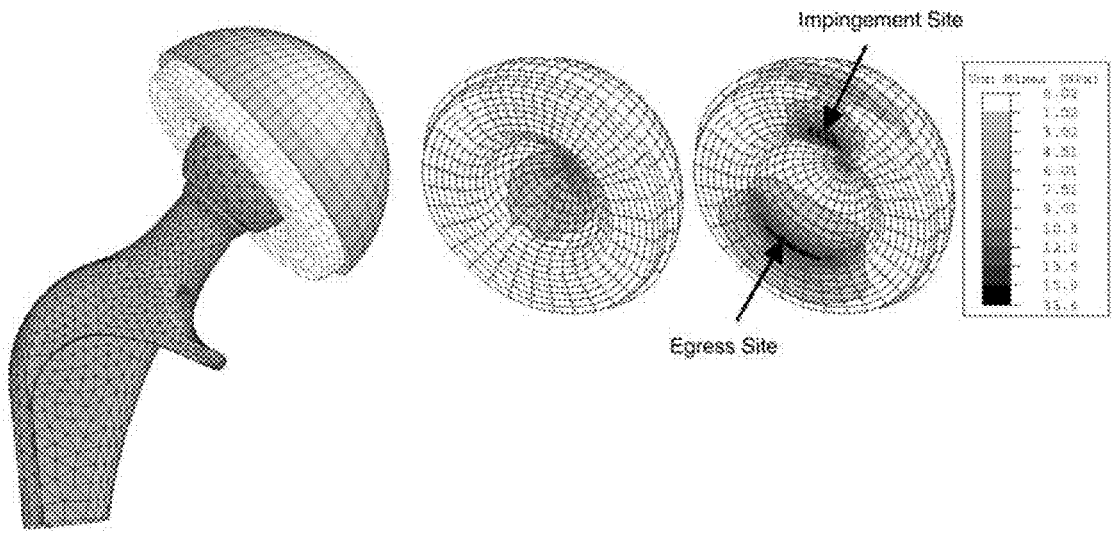

In this case the implant 1 is for a mammalian first carpometacarpal joint as shown in FIG. 1(a) for spacing a trapezium bone of the joint from a first metacarpal bone of the joint while allowing translational movement of the first metacarpal bone in relation to the trapezium bone. The distal part 110 is configured for intramedullary engagement with an end of the first metacarpal bone. The proximal part 120 has a curved saddle-shaped platform 122 with a proximal-facing surface 124 for sliding on or traversing the trapezium bone. An articulating coupling (e.g., ball-and-socket) comprises a neck 123 bridging the saddle 122 to a ball 121, as is known. This allows controlled articulation of the trapezium and first metacarpal bones.

Figure 5:
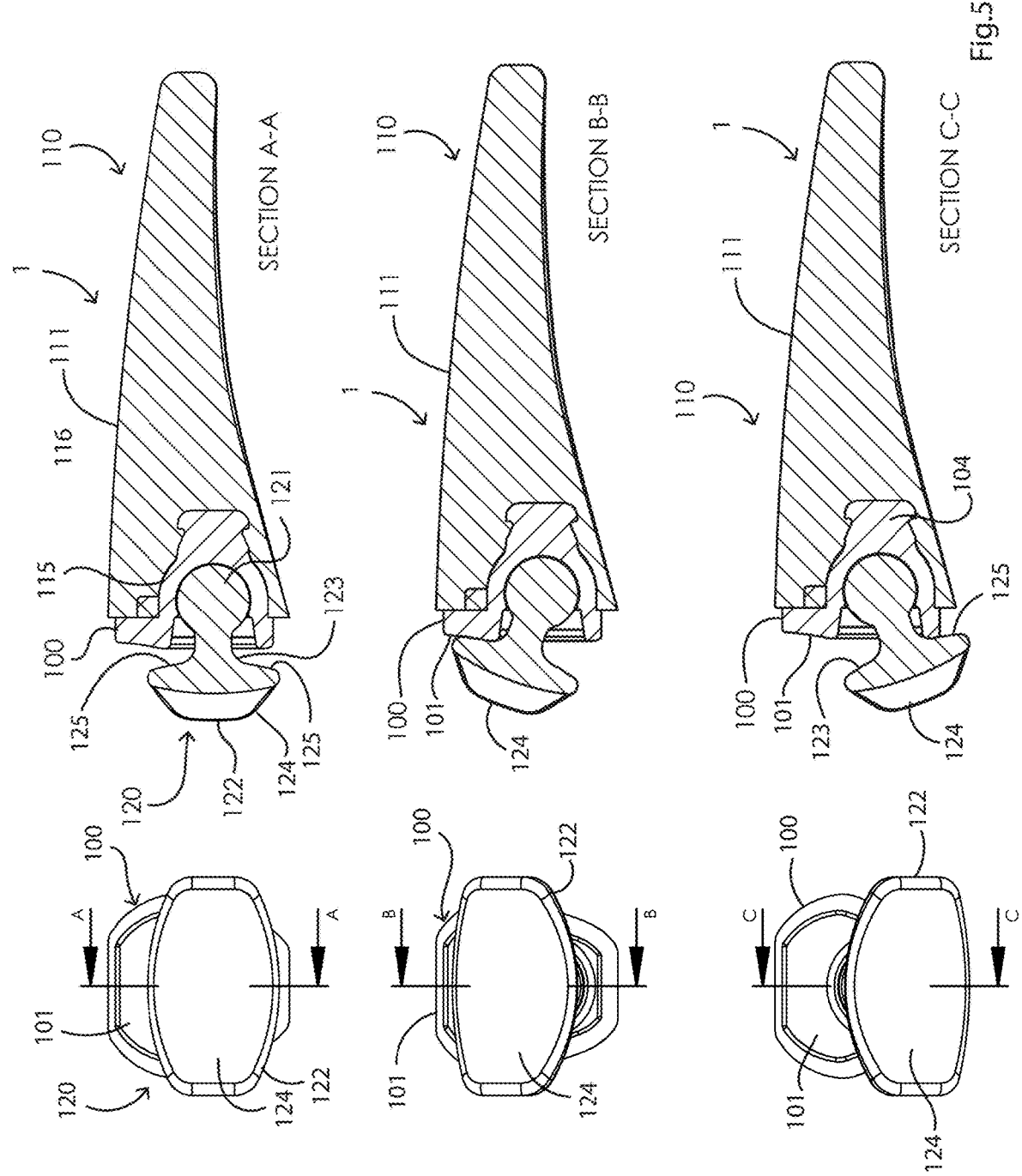
FIG. 5 is a set of three pairs of end and sectional views showing the implant at different relative positions between its proximal and distal parts.

The insert 100 has a buffer interface feature (i.e., buffer surface), in this case a flange 105 with a contoured proximally-facing surface 101, which may be annular as shown in FIG. 5. Distally of this surface there is a shoulder 102 which acts as a key for engaging the insert 100 in the stem 111 (see FIG. 5) and preventing rotation of the insert in the stem, and surrounding a socket 103 with a rim 106 to receive the articulated coupler ball 121. There is snap-fit engagement of the ball 121 (see especially FIG. 3(d) and FIG. 5) in the socket 103, behind the socket's rim 106, to enable the assembly of an articulating hemiarthroplasty intra-operatively, and it may also prevent disassembly of the device in vivo. The socket can be central or offset in any direction or angle as needed.

Further distally, the insert 100 comprises an annular locking rim 104 for snap-fitting into a corresponding groove 116 of the stem 111 recess 115 which accommodates the insert 100. Engagement of the insert 100 into the stem 111 is effective due to the resilience of the insert material and the fact that there is comprehensive surface-to-surface contact in a snap-fitting manner between the rim 104 and its corresponding engagement surface within the stem 111. This snap-fit engagement of the insert 100 and stem 111 enables the assembly of an articulating hemiarthroplasty intra-operatively, and it my also prevent disassembly of the device in vivo. The insert is keyed by the shoulder 102 to prevent rotation and potential consequent back side wear.

The flange 105 (and in this case the whole insert 100) is of a resilient polymer material which is preferably a polymer, such as UHMWPE (in any of its forms, possibly including vitamin E) or PEEK, in any of its forms. In such case, the insert 100 may be referred to as a unitary non-metallic wear member. It may alternatively be of other materials commonly used in orthopaedics such as Pyrocarbon (PyC), or ceramic depending on the wear patterns expected of the construct. The insert 100 is of a material which is different from the metal material of the unitary proximal part 120 (saddle 122, neck 123, and articulated coupler ball 121), hence avoiding any Galvanic-type interactions which may cause excessive wear and/or chemical reactions which give rise to contaminants. Likewise, the (polymer) material of the insert is different from the metal material of the stem 111 for the same reasons. In general metal-to-metal contact interfaces are avoided in the implant. While a polymer material is good for wear, the biomechanical advantages of the flange i.e., breaking up the two axes of rotation, may be more important, and as such the flange could possibly be made of any suitable material. An example would be where the insert (or "liner") is made of a ceramic material, but the head is made of PEEK, which would still enable a snap fit engagement for the articulating coupling. It is generally preferred that the flange and the socket are not of a relatively hard material as that might not permit a snap fit for anything other than a material with low modulus/high resilience. This may be the other way around, for example, if the head is a polymer and the liner is a ceramic, the soft polymer material may still snap fit into the hard ceramic socket.

Thus, as discussed above, the implant 1 may include at least one non-metallic wear surface. The non-metallic wear surface may be present on any portion of the implant where a surface of the stem 110 and a surface of the platform 122 may engage, as shown in FIG. 5. In the case when the stem 110 includes an insert 100, the insert 100 may include at least one non-metallic wear surface. The at least one non-metallic wear surface may include a shaped surface, for example a surface with a convex curvature, and/or may form an annular surface. The platform may include a distal end surface having a corresponding shape, for example concave. Alternatively, if the at least one non-metallic wear surface has a concave curvature, the platform may include a distal end surface having a convex curvature.

Figure 6:
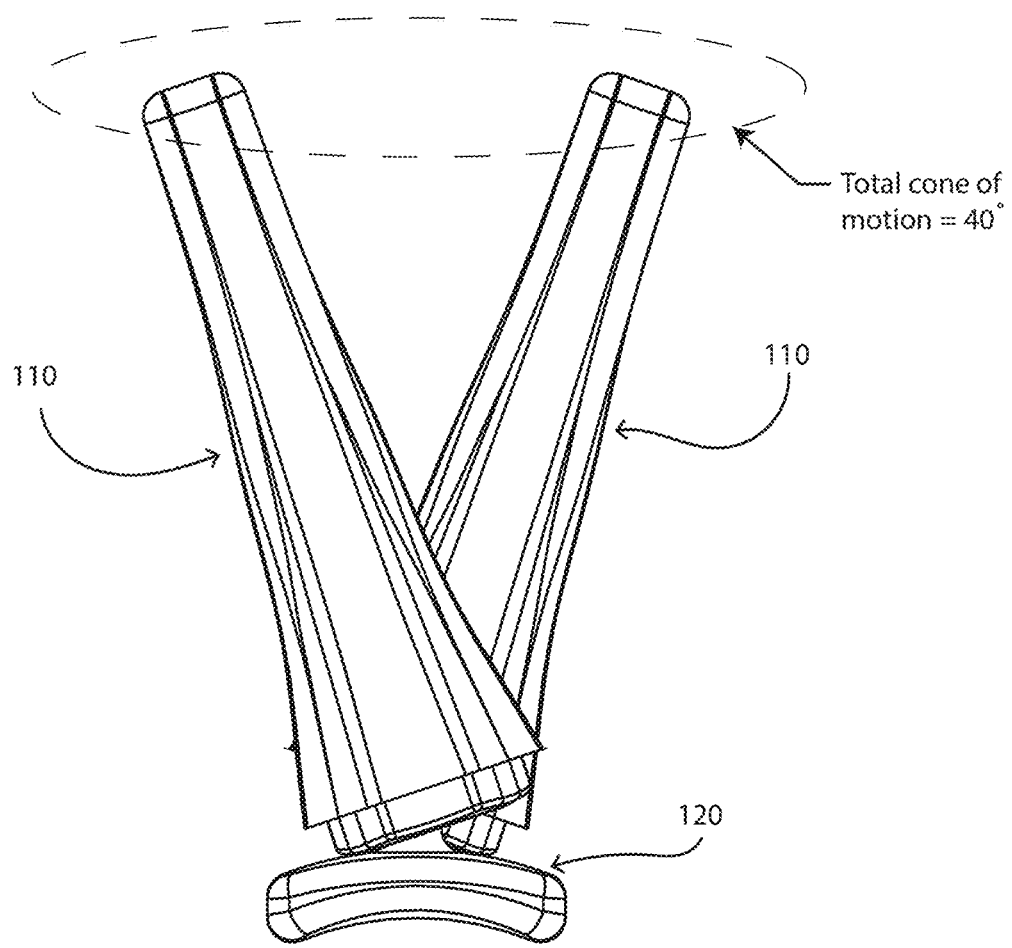
FIG. 6 is a diagram illustrating the allowed cone of motion between the proximal and distal parts.

The flange material resilience is preferably sufficient to allow compression in use, to an extent desired to achieve gradual conversion of motion between the axes. For this implant, for the thumb, the thickness of the flange 105 is preferably in the range of 0.5 mm to 4 mm, and preferably 1.0 mm to 3.0 mm. The implant may be provided as a kit in which there is the proximal part 122, the stem 111 of the distal part 110, and a range of two or more inserts each of which fits into the stem 111 but has a different flange thickness. The flange thickness sets the range of relative motion allowed, and in the example illustrated in FIG. 6 it is 40°. In general, the flange is preferably configured to provide a cone of motion in the range of 30° and 60° of the distal part about the proximal part. This allows the surgeon to choose the desired cone of motion. The implant thus achieves a predictable wear pattern. Also, decreasing the cone of motion reduces the chances of dislocation. It should be noted that for this type of joint, multi-axial, the full range of motion is actually about 80° when one takes into account the sliding motion of the proximal part over the trapezium bone. The illustration of FIG. 6 is based on the proximal part being static, for illustration purposes.

Moreover, the flange 105 contoured proximally-facing surface 101 is configured to match a corresponding mating distal surface 125 of the saddle 122, to cause the motion of forces between the two axes of motion to be limited in a step-wise manner, i.e., limiting movement between the parts 110 and 120. Hence, there is not an abrupt change in force, or "flip-flop" between the two axes. The mating surfaces 101 and 125 provide a large surface area for contact between the parts 110 and 120 as illustrated in FIGS. 5 and 7.

By having a load bearing surface 101 interposed between the axes, the forces are distributed in a more controlled, more natural, and more physiological manner. The relative motion around the articulated coupling is limited in one example to about 40°, as illustrated in FIG. 6. This extent of motion is sufficient for use of the implant after deployment, but it also helps to ensure that there are not excessive impact forces between the surfaces and there is a smooth transition between the axes shown in FIGS. 1(*a*) and 1(*b*).

The liner snap-fit element 104 enables easy and effective assembly into the stem 111. Also, the liner snap-fit socket 103 facilitates the capture of a mating ball to form the ball-and-socket joint in a manner which is advantageous because of the resilience of the material of the insert 100. As shown in the figures, the socket 103 may be spherically shaped to receive the ball of the ball-and-socket joint.

The flange 105 surface 101 is contoured to match the geometry of the head component to maximize surface contact and hence minimize liner wear.

The insert 100 is replaceable from within the stem, i.e., it can be removed, and another inserted in its place in the case of excessive wear. Insert 100 may be installed and/or removed with an appropriate tool or tool set.

The insert 100 advantageously limits the extent of relative rotation in the abduction-adduction and flexion-extension planes. As shown in FIGS. 5 and 6 the saddle 122 has less freedom to rotate upwardly in this view and when contact is made with the surface insert 100 there is full-surface contact between the saddle 122 and the contoured surface 101. Preferably, the flange's contoured surface is tapered radially and distally and the saddle's corresponding mating surface is tapered radially and proximally.

On the lower side as viewed in FIG. 5, there is a smaller meeting surface area, but the same effects and advantages apply. It will be appreciated that the insert 100 causes the impingement issue to be ameliorated.

Referring to FIGS. 7(*a*) and 7(*b*), the shaded areas receive maximum material stress between the ball and socket interface. In FIG. 7(*b*), the saddle 122 of proximal part 120 is not in contact with the flange 105 of insert 100. As a result, all of the material stresses are concentrated at the ball and socket interface (shown in FIG. 7(*b*) as the stress region on ball 121). FIG. 7(*a*) illustrates a portion of proximal part 120, e.g., the distally-facing side of the saddle 125, in contact with the flange 105 of insert 100 and proximally facing surface 101. This increased contact area, shown as an additional stress region in FIG. 7(*a*) allows for a wider distribution of material stresses. The insert 100 may be thickest at the portion with such increased contact area. This wider and more even distribution of stress load on the implant 1, reduces stress concentration at the ball and socket interface, shown at ball 121, and may prolong the life of the implant 1.

Alternative Examples

It is also envisaged that the implant may have a buffer interface (i.e., buffer surface) which includes a feature in addition to or instead of a flange, and/or which is not necessarily on an insert in the distal part. For example, the proximal part may have a buffer interface on the distal-facing surface, which interface engages the distal part with a large surface area. Such an interface may be a coating of a thickness in the range of 0.5 mm to 3.0 mm, and preferably 1.0 mm to 2.0 mm for example. The interface is preferably of a resilient material, such as any of the polymers mentioned in the description above. In this case it is envisaged that the distal part may not have a flange in some examples, in which case the proximal-part interface feature engages the distal part stem directly.

Referring to FIGS. 8(*a*) and 8(*b*) an implant 150 is also for a thumb and comprises a distal part with a stem 151 and an insert 152 to receive a ball 153 of a proximal part 154. The distally-facing side of the proximal part 154 has a buffer interface namely a coating 157. This is provided to achieve at least some of the benefits of the flange of the previous embodiments. The coating 157 provides a buffer effect which reduces the cone of motion and provides an increased surface area for distribution of forces across the construct.

It is envisaged that the implant distal part may include the physical features of the insert in an integral manner. Or, the flange 105 may be provided as a discrete item. Also, an insert could alternatively be threaded for engagement in the stem rather than being snap-fitted.

A stem with an integral flange may comprise a hard material and a coupling ball may be made of a softer material. The flange is in relation to the base of the stem and metacarpal bone.

The flange may be an integral part of the stem. It would preferably have the advantageous features of having a surface contoured to provide a large surface area for contact with the contacting part.

It is envisaged that there may alternatively be a resilient ball and a high modulus socket.

In examples above, the contour of the flange matches the distally-facing surface 125 of the saddle 122, however, the surfaces may be configured otherwise. For example, the distally-facing surface 125 of the saddle 122 may have a convex curvature as shown in the figures.

The distraction distance, i.e., the distance between two bones post-implantation of a device, can be modified by increasing the height of the saddle head as shown in FIGS. 5 and 6 for example. The cone of motion will not be affected as the flange will be of the same geometry. Alternatively, the flange can be thicker or thinner which will affect the cone of motion. In some clinical uses, for example, a patient who frequently dislocates an implant, a surgeon may choose during revision surgery to use a flanged insert with a very thick flange, to decrease the range of motion, potentially decreasing the likelihood of dislocation by increasing the jump distance (the distance a ball must move out of a socket in order to dislocate).

It is envisaged that the insert may be engaged in the stem without a mechanical/physical engagement feature, and may have only an adhesive bond.

Uniaxial Implant Examples

As noted in the Introduction with reference to FIGS. 1 (*c*) and (*d*), hip implants can have issues with impingement of the liner around the ball. We also describe an implant with a flange which may improve the outcomes of hip implants. FIG. 9 illustrates an implant 200 with a neck 210 with a ball, and a socket 202 having a flange 203 extending radially around the socket's entrance. The material of the flange 203 is of a resilient material such as UHMWPE, PEEK, ceramic or another material commonly used in orthopaedic implants. The flange 203 is part of a liner for the socket 202, and the liner is attached to the remainder of the socket (distal) part by snap fit, taper, or some other suitable locking mechanism. The flanged liner 203 has a geometry with an interfacing surface matching that of the impinging component, in this case the neck 201 below the ball. FIG. 9 shows two positions for the neck 201, showing that there is an angular freedom of movement of 110°. This arrangement ameliorates the impingement forces over the socket 202, dispersing stress forces across the interface surface 204 and helping to prevent dislocation. Hence the flange 203 not only provides a much larger interfacing/contacting surface 204, but it is also of a more resilient material so that contact forces are absorbed.

As noted above, while a polymer liner and metal ball is one preferred arrangement, there may alternatively be a metal liner and poly ball, a ceramic liner and poly ball, a poly liner and ceramic ball in any suitable combination depending on whether the wear pattern or biomechanical axis management is more important.

The material of the flange 203 is resilient, preferably a polymer such as UHMWPE, PEEK or ceramic. The insert is attached to the remainder of the socket part by press fit, threads, or snap fit. The distal part and proximal parts in total implants of the joints may be reversed depending on the joint and the implant.

The flange may be contoured to match the geometry of any part of a mating component. For example, in shoulder implants, the flange may be concave to mate optimally with the relative geometry of the neck of an implant. Similarly, in a hip implant, the flange may be convex to match the geometry of a neck component.

The invention is not limited to the embodiments described but may be varied in construction and detail.

The invention claimed is:

1. A bone joint implant for a mammalian first carpometacarpal joint, comprising:
    a proximal part configured for translational motion on the trapezium bone, the proximal part including a platform;
    a distal part configured for intramedullary engagement with an end of the first metacarpal bone, the distal part including a stem and an insert extending into a proximal end of the stem, the insert including a flange extending proximal of the proximal end of the stem; and
    an articulating coupling between the proximal and distal parts, and
    the flange including a proximal end surface limiting movement between the proximal part and the distal part.

2. The bone joint implant as claimed in claim 1, wherein the insert is non-metallic and the platform is metallic.

3. The bone joint implant as claimed in claim 2, wherein the proximal end surface of the flange has a concave curvature.

4. The bone joint implant as claimed in claim 3, wherein the platform includes a distal end surface having a convex curvature.

5. The bone joint implant as claimed in claim 4, wherein the flange is annular.

6. The bone joint implant as claimed in claim 1, wherein the articulating coupling is a ball and socket coupling, and the proximal part includes the ball, and the insert includes the socket.

7. The bone joint implant as claimed in claim 6, wherein the ball extends distally of the flange.

8. A bone joint implant for a mammalian first carpometacarpal joint, comprising:
    a proximal part configured for translational motion on the trapezium bone, the proximal part including a metallic platform having a proximal end surface having a concave curvature, and a distal end surface having a convex curvature;
    a distal part configured for intramedullary engagement with an end of the first metacarpal bone, the distal part including a metallic stem and a non-metallic insert extending into a proximal end of the stem, the insert including a flange extending proximal of the proximal end of the stem; and
    a ball and socket coupling between the proximal and distal parts, the proximal part including the ball, and the insert including the socket, and
    the flange including a proximal end surface limiting movement between the proximal part and the distal part.

9. The bone joint implant as claimed in claim 8, wherein the proximal end surface of the flange includes a concave surface.

10. The bone joint implant as claimed in claim 8, wherein the proximal end surface of the flange is annular.

* * * * *